(12) United States Patent
Al Mahmood

(10) Patent No.: US 8,470,997 B2
(45) Date of Patent: Jun. 25, 2013

(54) PHARMACEUTICAL COMPOSITION FOR PREVENTING, STABILISING AND/OR INHIBITING BLOOD AND LYMPH VASCULARIZATION

(75) Inventor: Salman Al Mahmood, Paris (FR)

(73) Assignee: Gene Signal International SA, Epalinges (CH)

( * ) Notice: Subject to any disclaimer, the term of this patent is extended or adjusted under 35 U.S.C. 154(b) by 316 days.

(21) Appl. No.: 12/700,851

(22) Filed: Feb. 5, 2010

(65) Prior Publication Data

US 2010/0305189 A1    Dec. 2, 2010

Related U.S. Application Data

(60) Provisional application No. 61/150,101, filed on Feb. 5, 2009.

(51) Int. Cl.
*C07H 21/04* (2006.01)
*A61K 31/70* (2006.01)

(52) U.S. Cl.
USPC ........................................... 536/24.5; 514/44

(58) Field of Classification Search
None
See application file for complete search history.

(56) References Cited

U.S. PATENT DOCUMENTS

| | | | |
|---|---|---|---|
| 4,136,173 A | 1/1979 | Pramoda et al. | |
| 4,136,177 A | 1/1979 | Lin et al. | |
| 4,136,178 A | 1/1979 | Lin et al. | |
| 4,861,760 A | 8/1989 | Mazuel et al. | |
| 5,212,162 A | 5/1993 | Missel et al. | |
| 7,417,033 B2 | 8/2008 | Al-Mahmood | |

FOREIGN PATENT DOCUMENTS

WO    02103014    12/2002

OTHER PUBLICATIONS

Berdugo, M. et al., "Downregulation of IRS-1 Expression Causes Inhibition of Corneal Angiogenesis", IOVS, Nov. 2005, pp. 4072-4078, vol. 46, No. 11, XP002532747.
Cursiefen, C., et al., "Eye Drops Inhibit Corneal Neovascularization and Regress: Interim Results of a Multicenter, Double-Blind, Randomized Phase II Study" Congress of the German Society of Opthalmology, Sep. 2008, Berlin, Germany, XP002532748, abstract only.
Cursiefen, C., et al, "Eye Drops, an Antisense Oligonucleotide Against IRS-1, Inhibit and Regress Corneal Neovascularization: Interim Results of a Muiticenter Double-Blind; Randomized Phase II Study", Congress of European society of Cataract and Refractive Surgeons, Sep. 2008 Berlin, Germany, XP002532749, abstract only.
Bock, F., et al, "Inhibition of Angiogenesis in the Anterior Chamber of the Eye", Ophthaimology, Apr. 2007, pp. 336-344, vol. 104, No. 4, Springer, XP00019515703, abstract only.
Al-Mahmood, S., et al., "Potent in Vivo Antiangiogenic Effects of GS-101 (5'TATCCGGAGGGCTCGCCATGCTGCT-3'), an Antiserise Oligonucleotide Preventing the Expression of Insulin Receptor Substrate-1", Jounal of Pharmacology and Experimental Therapeutics, May 2009, pp. 496-504, vol. 329, No. 2, XP008107310.
European Search Report dated Jun. 18, 2009 from corresponding EP09305107.

*Primary Examiner* — Tracy Vivlemore
(74) *Attorney, Agent, or Firm* — Young & Thompson

(57) ABSTRACT

A pharmaceutical composition including as active agent, an antisens oligonucleotide having the sequence SEQ ID NO: 1 in a concentration from about 0.40 mg/ml to about 2 mg/ml and the use thereof for preventing, stabilizing and/or inhibiting blood and lymph vascularization.

20 Claims, 2 Drawing Sheets

SEQUENCE LISTING

<160> NUMBER OF SEQ ID NOS: 20

<210> SEQ ID NO 1
<211> LENGTH: 25
<212> TYPE: DNA
<213> ORGANISM: artificial
<220> FEATURE:
<223> OTHER INFORMATION: antisense oligonucleotide

<400> SEQUENCE: 1
tctccggagg gctcgccatg ctgct                                           25

```
<210> SEQ ID NO 2
<211> LENGTH: 25
<212> TYPE: DNA
<213> ORGANISM: artificial
<220> FEATURE:
<223> OTHER INFORMATION: oligonucleotide antisense

<400> SEQUENCE: 2
tatccggagg gctcgccatg ctgct                                      25

<210> SEQ ID NO 3
<211> LENGTH: 24
<212> TYPE: DNA
<213> ORGANISM: artificial
<220> FEATURE:
<223> OTHER INFORMATION: antisense oligonucleotide

<400> SEQUENCE: 3
tctccggagg gctcgccatg ctgc                                       24

<210> SEQ ID NO 4
<211> LENGTH: 23
<212> TYPE: DNA
<213> ORGANISM: artificial
<220> FEATURE:
<223> OTHER INFORMATION: antisense oligonucleotide

<400> SEQUENCE: 4
tctccggagg gctcgccatg ctg                                        23

<210> SEQ ID NO 5
<211> LENGTH: 22
<212> TYPE: DNA
<213> ORGANISM: artificial
<220> FEATURE:
<223> OTHER INFORMATION: antisense oligonucleotide

<400> SEQUENCE: 5
tctccggagg gctcgccatg ct                                         22

<210> SEQ ID NO 6
<211> LENGTH: 21
<212> TYPE: DNA
<213> ORGANISM: artificial
<220> FEATURE:
<223> OTHER INFORMATION: antisense oligonucleotide

<400> SEQUENCE: 6
tctccggagg gctcgccatg c                                          21

<210> SEQ ID NO 7
<211> LENGTH: 20
<212> TYPE: DNA
<213> ORGANISM: artificial
<220> FEATURE:
<223> OTHER INFORMATION: antisense oligonucleotide

<400> SEQUENCE: 7
tctccggagg gctcgccatg                                            20

<210> SEQ ID NO 8
<211> LENGTH: 19
<212> TYPE: DNA
<213> ORGANISM: artificial
<220> FEATURE:
<223> OTHER INFORMATION: antisense oligonucleotide

<400> SEQUENCE: 8
```

-continued tctccggagg gctcgccat                                         19

<210> SEQ ID NO 9
<211> LENGTH: 24
<212> TYPE: DNA
<213> ORGANISM: artificial
<220> FEATURE:
<223> OTHER INFORMATION: antisense oligonucleotide

<400> SEQUENCE: 9
ctccggaggg ctcgccatgc tgct                                   24

<210> SEQ ID NO 10
<211> LENGTH: 23
<212> TYPE: DNA
<213> ORGANISM: artificial
<220> FEATURE:
<223> OTHER INFORMATION: antisense oligonucleotide

<400> SEQUENCE: 10 tccgagggc tcgccatgct gct                                     23

<210> SEQ ID NO 11
<211> LENGTH: 22
<212> TYPE: DNA
<213> ORGANISM: artificial
<220> FEATURE:
<223> OTHER INFORMATION: antisense oligonucleotide

<400> SEQUENCE: 11
ccggagggct cgccatgctg ct                                     22

<210> SEQ ID NO 12
<211> LENGTH: 21
<212> TYPE: DNA
<213> ORGANISM: artificial
<220> FEATURE:
<223> OTHER INFORMATION: antisense oligonucleotide

<400> SEQUENCE: 12
cggagggctc gccatgctgc t                                      21

<210> SEQ ID NO 13
<211> LENGTH: 20
<212> TYPE: DNA
<213> ORGANISM: artificial
<220> FEATURE:
<223> OTHER INFORMATION: antisense oligonucleotide

<400> SEQUENCE: 13
ggagggctcg ccatgctgct                                        20

<210> SEQ ID NO 14
<211> LENGTH: 19
<212> TYPE: DNA
<213> ORGANISM: artificial
<220> FEATURE:
<223> OTHER INFORMATION: antisense oligonucleotide

<400> SEQUENCE: 14
gagggctcgc catgctgct                                         19

<210> SEQ ID NO 15
<211> LENGTH: 18
<212> TYPE: DNA
<213> ORGANISM: artificial

```
<220> FEATURE:
<223> OTHER INFORMATION: antisense oligonucleotide

<400> SEQUENCE: 15
agggctcgcc atgctgct                                                     18

<210> SEQ ID NO 16
<211> LENGTH: 16
<212> TYPE: DNA
<213> ORGANISM: artificial
<220> FEATURE:
<223> OTHER INFORMATION: antisense oligonucleotide

<400> SEQUENCE: 16
ggctcgccat gctgct                                                       16

<210> SEQ ID NO 17
<211> LENGTH: 15
<212> TYPE: DNA
<213> ORGANISM: artificial
<220> FEATURE:
<223> OTHER INFORMATION: antisense oligonucleotide

<400> SEQUENCE: 17
gctcgccatg ctgct                                                        15

<210> SEQ ID NO 18
<211> LENGTH: 14
<212> TYPE: DNA
<213> ORGANISM: artificial
<220> FEATURE:
<223> OTHER INFORMATION: antisense oligonucleotide

<400> SEQUENCE: 18
ctcgccatgc tgct                                                         14

<210> SEQ ID NO 19
<211> LENGTH: 13
<212> TYPE: DNA
<213> ORGANISM: artificial
<220> FEATURE:
<223> OTHER INFORMATION: antisense oligonucleotide

<400> SEQUENCE: 19
tcgccatgct gct                                                          13

<210> SEQ ID NO 20
<211> LENGTH: 12
<212> TYPE: DNA
<213> ORGANISM: artificial
<220> FEATURE:
<223> OTHER INFORMATION: antisense oligonucleotide

<400> SEQUENCE: 20
cgccatgctg ct                                                           12
```

PHARMACEUTICAL COMPOSITION FOR PREVENTING, STABILISING AND/OR INHIBITING BLOOD AND LYMPH VASCULARIZATION

FIELD OF THE INVENTION

The file of this patent contains at least one drawing executed in color. Copies of this patent with color drawings will be provided by the Patent and Trademark Office upon request and payment of the necessary fee.

The present invention relates to a stable ophthalmic composition containing an antisense oligonucleotide GS-101, capable of inhibiting the expression of the insulin receptor substrate-1 (IRS-1) and inhibiting formation of capillary tubes for the treatment of inflammation of the eyes.

BACKGROUND OF THE INVENTION

Angiogenesis is a fundamental process by means of which new blood vessels are formed. This process is essential in multiple normal physiological phenomena such as reproduction, development and even cicatrisation.

The formation of neovessels by endothelial cells, involves the migration, growth and differentiation of endothelial cells. Regulation of these biological phenomena is linked to Insulin receptor substrate 1 (IRS-1), which is a cytoplasmic docking protein that functions as an essential signalling intermediate downstream of activated cell surface receptors, including insulin, insulin-like growth factor 1 (IGF-1), prolactin, growth hormone (GH), vascular endothelial growth factor (VEGFA) receptors, members of the integrin receptor family, and select cytokine receptors.

The normal cornea is devoid of both blood and lymphatic vessels. This avascularity is evolutionary highly conserved to maintain transparency and visual acuity. Nonetheless due to a variety of severe inflammatory diseases the cornea can become invaded by pathologic blood and lymphatic vessels. Inflammatory diseases of the eye, usually linked to pathologic corneal neovascularization, not only reduce corneal transparency, but also are a major risk factor for corneal transplantation.

Those inflammatory diseases of the eyes can be initiated by contact lens misuse, pseudomonas keratitis, herpes simplex keratitis, herpes zoster keratitis, Fuchs-Stevens-Johnson syndrome, prior surgery, alkali burns, graft rejection, degenerative disorders, as well as exposure to ultraviolet light such as sunlight or sunlamps, exposure to other intense light sources such as welding arcs or snow or water reflections, dry eyes caused by an eyelid disorder or insufficient tear formation, a foreign object in the eye, a vitamin A deficiency, or a reaction to eyedrops, eye cosmetics, pollution, or airborne particles such as dust, pollen, mold, or yeast.

In addition, host corneal neovascularization (both pre- as well as post-operatively) is one of the strongest risk factors for subsequent immune rejections after corneal grafting. Corneal graft rejection is primarily a cell-mediated immune response controlled by T cells. Normal corneal immune privilege can be eroded by neovascularisation, especially if accompanied by the sequelae of ocular inflammation and raised intraocular pressure. This is because if neovascularisation is present either before or after a corneal graft, the growth of new blood vessels provides a route of entry for immune-mediating cells to the graft, while the growth of new lymphatic vessels enables the exit of APCs and antigenic material from the graft to regional lymph nodes. The cornea consequently becomes infiltrated with and sensitized to immune reaction mediators. Therefore, although not an immune reaction in itself neovascularisation induces an immune response that can lead to immunological corneal graft rejection.

Conventional therapy, based on corticoids and immunosuppressants, is only partly effective in inhibiting corneal neovascularization. Corticosteroids and immunosuppressive therapy are used but are not very effective and have numerous side effects. There is therefore a need for alternative therapeutic approaches. The inventors previously described in U.S. Pat. No. 7,417,033 a pharmaceutical composition comprising the antisense oligonucleotide GS-101.

GS-101 is a 25 mer phosphorothioate with a molecular weight of 8,036 Da of the following sequence:

5'-TCTCCGGAGGGCTCGCCATGCTGCT-3'    (SEQ ID NO: 1)

There was still a need to define more precisely the dose and regimen at which said pharmaceutical composition is tolerable, efficient and optimal for preventing, stabilizing and/or inhibiting blood and lymph vascularization in a subject in need thereof.

SUMMARY OF THE INVENTION

One object of the invention is a pharmaceutical composition comprising as active agent, an antisens oligonucleotide having the sequence SEQ ID NO: 1, wherein said antisens oligonucleotide is in a concentration from about 0.40 mg/ml to about 2 mg/ml.

In one embodiment, said antisens oligonucleotide is in a concentration from about 0.80 mg/ml to about 1 mg/ml.

In another embodiment, said pharmaceutical composition is in the form of an aqueous solution, an ointment, micelles or an emulsion.

In another embodiment, said pharmaceutical composition is for preventing, stabilizing or inhibiting blood and lymph vascularization.

In another embodiment, said pharmaceutical composition is for treating corneal graft rejection, glaucoma, retinopathy, retinopathy of prematurity, age related macular degeneration and diabetic retinopathy.

In another embodiment, said pharmaceutical composition is to be administrated topically, by intravitreal injection or by intraconjunctivial injection.

In another embodiment, said pharmaceutical composition is to be administrated in the form of eye drop once, twice, or more per day.

In another embodiment, the amount of antisens oligonucleotide in the pharmaceutical composition to be administrated daily per eye is from about 8 μg to about 40 μg.

In another embodiment, the amount of antisens oligonucleotide in the pharmaceutical composition to be administrated daily per eye is from about 40 μg to about 100 μg per drop.

Another object of the invention is a unit dose container comprising the pharmaceutical composition as described here above In one embodiment, said unit dose is capable of dispensing eye drops.

DETAILED DESCRIPTION OF THE INVENTION

One object of the invention is a pharmaceutical composition comprising as active agent, an antisense oligonucleotide having the sequence SEQ ID NO: 1, wherein said antisens oligonucleotide is in a concentration from about 0.40 mg/ml to about 2 mg/ml.

Said antisense oligonucleotide has for nucleic sequence the sequence SEQ ID NO: 1

```
5'-TCTCCGGAGGGCTCGCCATGCTGCT-3'
``` or any function conservative sequence comprising from 9 to 30 nucleotides that has 75%, 80%, 85%, 90%, 95% or more than 95%, 96%, 97%, 98%, 99% of identity compared to SEQ ID NO: 1 and that conserves the capacity of inhibiting IRS-1 gene expression as SEQ ID NO: 1. Said function conservative sequence comprising 9 to 30 nucleotides may be a sequence comprising SEQ ID NO: 1 or SEQ ID NO: 2 between other nucleic acids in C-terminal and N-terminal. Said function conservative sequence may also be a 9 to 12 contiguous nucleotides fragment of SEQ ID NO: 1 or SEQ ID NO: 2.

An example of a function conservative sequence of SEQ ID NO: 1 is SEQ ID NO: 2 (5'-TATCCGGAGGGCTCGCCATGCTGCT-3'). Other examples of a function conservative sequence of SEQ ID NO: 1 are the following sequences:

```
5'-TCTCCGGAGGGCTCGCCATGCTGC-3'    (SEQ ID NO: 3)
5'-TCTCCGGAGGGCTCGCCATGCTG-3'     (SEQ ID NO: 4)
5'-TCTCCGGAGGGCTCGCCATGCT-3'      (SEQ ID NO: 5)
5'-TCTCCGGAGGGCTCGCCATGC-3'       (SEQ ID NO: 6)
5'-TCTCCGGAGGGCTCGCCATG-3'        (SEQ ID NO: 7)
5'-TCTCCGGAGGGCTCGCCAT-3'         (SEQ ID NO: 8)
5'-CTCCGGAGGGCTCGCCATGCTGCT-3'    (SEQ ID NO: 9)
5'-TCCGGAGGGCTCGCCATGCTGCT-3'     (SEQ ID NO: 10)
5'-CCGGAGGGCTCGCCATGCTGCT-3'      (SEQ ID NO: 11)
5'-CGGAGGGCTCGCCATGCTGCT-3'       (SEQ ID NO: 12)
5'-GGAGGGCTCGCCATGCTGCT-3'        (SEQ ID NO: 13)
5'-GAGGGCTCGCCATGCTGCT-3'         (SEQ ID NO: 14)
5'-AGGGCTCGCCATGCTGCT-3'          (SEQ ID NO: 15)
5'-GGGCTCGCCATGCTGCT-3'           (SEQ ID NO: 16)
5'-GCTCGCCATGCTGCT-3'             (SEQ ID NO: 17)
5'-CTCGCCATGCTGCT-3'              (SEQ ID NO: 18)
5'-TCGCCATGCTGCT-3'               (SEQ ID NO: 19)
5'-CGCCATGCTGCT-3'                (SEQ ID NO: 20)
```

Said antisense oligonucleotides may be synthesized by all methods well known by the person skilled in the art, such as chemical synthesis.

In one embodiment, said pharmaceutical composition comprises from 0.50 mg/ml to 1.75 mg/ml of said antisense oligonucleotide.

In another embodiment, said pharmaceutical composition comprises from about 0.60 mg/ml to about 1.5 mg/ml of said antisense oligonucleotide.

In another embodiment, said pharmaceutical composition comprises from about 0.70 mg/ml to about 1.25 mg/ml of said antisense oligonucleotide.

In another embodiment, said pharmaceutical composition comprises from about 0.80 mg/ml to about 1 mg/ml of said antisense oligonucleotide.

In another embodiment, said pharmaceutical composition comprises from about 0.8 mg/ml to about 0.90 mg/ml of said antisense oligonucleotide.

In one embodiment, said pharmaceutical composition comprises from about 0.40 mg/ml to about 0.50 mg/ml of said antisense oligonucleotide, preferably from about 0.43 mg/ml.

In another embodiment, said pharmaceutical composition comprises from about 0.80 mg/ml to about 0.90 mg/ml of said antisense oligonucleotide, preferably from about 0.86 mg/ml.

Another object of the invention is the pharmaceutical composition as described here above for preventing, stabilizing or inhibiting blood and lymph vascularization or for use in preventing, stabilizing and/or inhibiting blood and lymph vascularization.

Another object of the invention is a method for preventing, stabilizing and/or inhibiting blood and lymph vascularization in a subject in need thereof, comprising administering to said subject a pharmaceutical composition as described hereabove.

In one embodiment, the pharmaceutical composition as described here above is useful for preventing, stabilizing and/or inhibiting blood and lymph vascularization in the cornea, in the anterior chamber of the eye, in the posterior chamber of the eye, in the macula, in the retina and/or in the choroid.

As used herein, the term "subject" refers to a mammal, preferably a human, but also can refer to animals, for example, cats, dogs, mice, cows, horses, pigs, and the like. Especially, the invention aims at addressing blood and lymph neovascularization.

Also, a specific object of the invention is prevention, stabilization and/or inhibition of corneal angiogenesis, especially corneal vascularization or corneal neovascularization.

The pharmaceutical composition of the invention may be formulated into a variety of topically or injectable administrable ophthalmic compositions, such as solutions, suspensions, gels, ointments, micelles and emulsions such as water-in-oil emulsion or oil-in-water emulsion, the emulsion being cationic or anionic.

A liquid which is ophthalmically acceptable is formulated such that it can be administered topically to the eye. The comfort should be maximized as much as practicable, although sometimes formulation considerations (e.g. drug stability, bioavailability, etc.) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

Usually, said ophthalmic pharmaceutical composition is sterile.

For ophthalmic application, solutions or medicaments are often prepared using a physiological saline solution as a major vehicle. Ophthalmic solutions are often maintained at a comfortable pH (usually within the range of pH 5.5-8) and an ophthalmically acceptable osmolality (generally about 150-450 mOsm, preferably 250-350 mOsm).

The formulations may also contain conventional, pharmaceutically acceptable preservatives, stabilizers and surfactants.

Various buffers and means for adjusting pH may be used so long as the resulting preparation is ophthalmically acceptable. Accordingly, buffers include, but are not limited to, acetate buffers, citrate buffers, phosphate buffers and borate buffers. Acids or bases may be used to adjust the pH of these formulations as needed.

In another embodiment, the composition contains a preservative. Preservatives that may be used in the pharmaceutical compositions disclosed herein include, but are not limited to, cationic preservatives such as quaternary ammonium compounds including benzalkonium chloride, polyquad, and the like; guanidine-based preservatives including PHMB, chlorhexidine, and the like; chlorobutanol; mercury preservatives such as thimerosal, phenylmercuric acetate and phenylmercuric nitrate; and oxidizing preservatives such as stabilized oxychloro complexes.

In another embodiment, the composition contains a surfactant. A surfactant may be used for assisting in dissolving an excipient or an active agent, dispersing a solid or liquid in a composition, enhancing wetting, modifying drop size, or a number of other purposes. Useful surfactants include, but are not limited to surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal & veg.); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated & ethoxylated fatty acids, alcohols, or alkyl phenols; protein-based surfactants; sarcosine derivatives; sorbitan derivatives; sucrose and glucose esters and derivatives.

In particular, ethoxylate surfactants are useful. An ethoxylate surfactants is one that comprises the moiety —O(CH2CH2O)n-OH, wherein n is at least about 1.

In one embodiment n is from about 1 to about 10,000. In another embodiment, n is from 1 to about 1000. In another embodiment, n is from about 1 to about 500. Some ethoxylates contain one ethoxylate moiety. In other words, there is a single ethoxylate chain on each molecule.

Examples of surfactants with one ethoxylate moiety, include, but are not limited to Ethoxylated alcohols wherein the alcohol has a single hydroxyl unit; alkylphenol ethoxylates; ethoxylated fatty acids; fatty acid methyl ester ethoxylates; polyethylene glycols; and the like.

Ethoxylates may comprise more than one ethoxylate moiety. In other words, there may be ethoxylate moieties attached to several different parts of the molecule. Examples include, but are not limited to: block polymers; ethoxylated oils; sorbitan derivatives; sucrose and glucose ethoxylates; and the like.

Block Polymers are polymers with the structure A-B-A', wherein A and A' are polyethylene chains of 1 or more ethylene units, and B is a polypropylene chain of one or more propylene units. Generally, but not necessarily, A and A' are approximately the same length.

In one embodiment, A and A' contain from about 2 to about 200 ethylene units. In another embodiment, A and A' contain from about 5 to about 100 ethylene units. In another embodiment, A and A' contain about 7 to about 15 ethylene units. In another embodiment, A and A' contain about 7, about 8, or about 12 ethylene units. In another embodiment, B contains from about 25 to about 100 propylene units. In another embodiment, B contains from about 30 to about 55 propylene units. In another embodiment, B contains about 30, about 34, or about 54 propylene units. In another embodiment, the molecular weight is from about 1000 to about 20000. In another embodiment, the molecular weight is from about 2000 to about 10000. In another embodiment, the molecular weight is about 2500, about 3000, about 3800, or about 8400.

Block Polymers include but are not limited to:
Poloxalene: wherein A has about 12 ethylene oxide units, B has about 34 propylene oxide units, A' has about 12 ethylene oxide units, and the average molecular weight is about 3000.

Poloxamer 182: wherein A has about 8 ethylene oxide units, B has about 30 propylene oxide units, A' has about 8 ethylene oxide units, and the average molecular weight is about 2500.

Poloxamer 188: wherein A has about 75 ethylene oxide units, B has about 30 propylene oxide units, A' has about 75 ethylene oxide units, and the average molecular weight is about 8400.

Poloxamer 331: wherein A has about 7 ethylene oxide units, B has about 54 propylene oxide units, A' has about 7 ethylene oxide units, and the average molecular weight is about 3800.

Ethoxylated Alcohols include but are not limited to:

Ethoxylates of linear alcohols having from about 6 to about 20 carbon atoms. In one embodiment, the linear alcohol has from about 10 to about 16 carbon atoms. In another embodiment, n is from about 1 to about 100. In another embodiment, n is from about 1 to about 50. In another embodiment, n is from about 5 to about 50 ethylene oxide units. In another embodiment, n is from about 1 to about 20 ethylene oxide units. In another embodiment, n is from about 30 to about 50 ethylene oxide units.

Ethoxylated Alkylphenols which are alkylphenols that are ethoxylated, i.e. the phenolic OH is replaced with an ethoxylate moiety. These include but are not limited to: octylphenol ethoxylate, i.e. C8H17Ph(OCH2CH2O) nH. nonylphenol ethoxylate, i.e. C9H19Ph (OCH2CH2O)nH. alkyphenols of the above formula wherein n is from about 1 to about 100.

Ethoxylated Fatty Acids, which include but are not limited to: ethoxylates which are esterified to form either: monoesters, i.e. RCO2 (CH2CH2O)nOH, where RCO2H is a fatty acid; or diesters, i.e. RCO2 (CH2CH2O)nC(=O)R. Fatty acids include, but are not limited to: (1) saturated fatty acids, which have no C=C moieties and include myristic acid, palmitic acid, stearic acid, arachidic acid, behenic acid, lignoceric acid; and (2) unsaturated fatty acids, including the following: monounsaturated fatty acids, which have one C=C group such as palmitoleic acid, oleic acid, and nervonic acid; diunsaturated fatty acids, which have two C=C groups, such as linoleic acid; triiunsaturated fatty acids, which have three C=C groups, such as [alpha]-linolenic acid and [gamma]-linolenic acid; tetraunsaturated fatty acids, which have four C=C groups, such as arachidonic acid; and pentaunsaturated fatty acids, which have five C=C groups, such as eicosapentaenoic acid. The following may also be used: Laurie Acid; 14 carbon fatty acids such as myristic acid; 16 carbon fatty acids such as palmitic and palmitoleic acid; 18 carbon fatty acids such as stearic acid, oleic acid, linoleic acid, [alpha]-linolenic acid, and [gamma]-linolenic acid; 20 carbon fatty acids such as eicosapentaenoic acid; 22 carbon fatty acids such as arachidic acid; and 24 carbon carbon fatty acids such as lignoceric acid and nervonic acid.

Ethoxylated Fatty Esters or Oils (Animal & Veg.) are products which result from reacting ethylene oxide with a fatty ester or an oil. When a fatty oil is used, the products is a mixture of ethoxylates of the fatty acids present in the oil, ethoxylates of glycerine, ethoxylates of mono and diglycerides, and the like. Specific examples include, but are not limited to: Ethoxylates of the following oils: Anise oil, Castor oil, Clove oil, Cassia oil, Cinnamon oil; Almond oil, Corn oil, Arachis oil, Cottonseed oil, Safflower oil, Maize oil, Linseed oil, Rapeseed oil, Soybean oil, Olive oil, Caraway oil, Rosemary oil, Peanut oil, Peppermint oil, Sunflower oil, Eucalyptus oil and Sesame oil; Coriander oil, Lavender oil, Citronella oil, Juniper oil, Lemon oil, Orange oil, Clary sage oil, Nutmeg oil, Tea tree oil, coconut oil, tallow oil, and lard. In one embodiment, from 1 to about 50 moles of ethylene oxide is used per mole of the oil triglyceride. In another embodiment, from about 30 to about 40 moles of ethylene oxide is used per mole of the oil triglyceride.

Ethylene oxide may also react with a fatty acid ester with a formula RCO2R' to form RCO2(CH2CH2O)nR'. Thus, surfactants having the formula RCO2(CH2CH2O)nR', where RCO2H is a fatty acid and R' is alkyl having from 1 to 6 carbons are contemplated. One embodiment is a fatty acid methyl ester ethoxylate, wherein R' is methyl.

In another embodiment, RCO2H is Lauric Acid; a 14 carbon fatty acid such as myristic acid; a 16 carbon fatty acid such as palmitic and palmitoleic acid; an 18 carbon fatty acids such as stearic acid, oleic acid, linoleic acid, [alpha]-linolenic acid, and [gamma]-linolenic acid; a 20 carbon fatty acids such as eicosapentaenoic acid; a 22 carbon fatty acids such as arachidic acid; or a 24 carbon carbon fatty acids such as lignoceric acid and nervonic acid. Polyethylene Glycols are ethoxylates that are unsubstituted, or terminated with oxygen on both ends, i.e. HO(CH2CH2O)nH, Sorbitan Derivatives are ethoxylated sorbates having a fatty acid capping one or more of the ethoxylated chains. These include but are not limited to: (A) sorbitan derivatives wherein the total number of ethylene oxide units is from 3 to 30; (B) sorbitan derivatives wherein the total number of ethylene oxide units is 4, 5, or 20; (C) sorbitan derivatives wherein the capping acid is laurate, palmitate, stearate, or oleate; The sorbitan derivative may be a POE sorbitan monolaurate; a POE sorbitan dilaurate; a POE sorbitan trilaurate; a POE sorbitan monopalmitate; a POE sorbitan dipalmitate; a POE sorbitan tripalmitate; a POE sorbitan monostearate; a POE sorbitan distearate; a POE sorbitan tristearate; a POE sorbitan monooleate; a POE sorbitan dioleate; or a POE sorbitan trioleate; Specific examples include: POE (20) sorbitan monolaurate; POE (4) sorbitan monolaurate; POE (20) sorbitan monopalmitate; POE (20) monostearate; POE (20) sorbitan monostearate; POE (4) sorbitan monostearate; POE (20) sorbitan tristearate; POE (20) sorbitan monoleate; POE (20) sorbitan 15 monoleate; POE (5) sorbitan 10 monoleate; POE (20) sorbitan trioleate.

Sucrose and Glucose Esters and Derivatives include, but are not limited to, polyvinyl alcohol, povidone, hydroxypropyl methyl cellulose, poloxamers, carboxymethyl cellulose, hydroxyethyl cellulose, and acrylates (e.g. Pemulen(R)).

Tonicity adjustors may be added as needed or convenient. They include, but are not limited to, salts, particularly sodium chloride, potassium chloride, mannitol and glycerin, or any other suitable ophthalmically acceptable tonicity adjustor.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The present compositions in the form of aqueous suspensions may include excipients suitable for the manufacture of aqueous suspensions. Such excipients are suspending agents, for example, sodium carboxymethylcellulose, methylcellulose, hydroxypropyl-methylcellulose, sodium alginate, polyvinylpyrrolidone, gun tragacanth and gun acacia; dispersing or wetting agents may be a naturally occurring phosphatide, for example, lecithin, or condensation products of ethylene oxide with long chain aliphatic alcohols, for example, hepta-deca-ethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof.

The present compositions in the form of oily suspensions may be formulated in a vegetable oil, for example, olive oil, castor oil, soy oil, sesame oil or coconut oil, or in a mineral oil such as liquid paraffin. Such suspensions may contain a thickening agent, for example beeswax, hard paraffin or cetyl alcohol.

The present compositions may also be in the form of oil-in-water emulsions. The oily phase may be a vegetable oil, for example, castor oil, olive oil, soy oil, or arachis oil, or a mineral oil, for example, liquid paraffin, and the like and mixtures thereof. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate.

Also included within the scope of this invention are preserved compounds which increase in viscosity upon administration to the eye. For example, "gelling polysaccharides" which are disclosed in U.S. Pat. No. 5,212,162, which is incorporated in its entirety herein by reference.

Also disclosed in this patent are ophthalmic formulations containing carrageenans and furcellarans which are administered as partially gelled liquids which gel upon instillation into the eye. Additionally, U.S. Pat. Nos. 4,136,173, 4,136,177, and 4,136,178, disclose the use of therapeutic compositions containing xanthan gum and locust bean gum which are delivered in liquid form to the eye and which gel upon instillation. U.S. Pat. No. 4,861,760 discloses opthalmological compositions containing gellan gum which are administered to the eye as non-gelled liquids and which gel upon instillation. Each of these four patents is incorporated in its entirety herein by reference. Also within the scope of this invention are preserved oils, ointments, gels and the like.

In one embodiment, the composition is formulated in accordance with routine procedures as a pharmaceutical composition adapted for topical administration to human beings.

In another embodiment, the composition is formulated in accordance with routine procedures as a pharmaceutical composition adapted for intraconjunctivial injection to human beings.

In another embodiment, the composition is formulated in accordance with routine procedures as a pharmaceutical composition adapted for intravitreal injection to human beings.

In one embodiment of the invention, said pharmaceutical composition as described here above is packaged in the form of unit dose.

In one embodiment, said unit dose is a container capable of dispensing eye drops such as common manual bulb-operated pipette or small squeeze bottle with a dropper tip.

In another embodiment, said unit dose is a container to which a device for the placement of eye drops may be applied.

In another embodiment, said unit dose is a container capable of atomizing drops or droplets.

In another embodiment, said unit dose is a disposable syringe.

In one embodiment of the invention, the amount of said antisense oligonucleotide to be administrated per eye per day is from about 8 to about 40 µg to prevent, stabilize and/or inhibit lymph and blood vascularization or corneal angiogenesis.

In one embodiment, the amount of said antisense oligonucleotide to be administrated per eye per day is from about 10 to about 35 µg.

In another embodiment, the amount of said antisense oligonucleotide to be administrated per eye per day is from about 12 to about 30 µg.

In another embodiment, the amount of said antisense oligonucleotide to be administrated per eye per day is from about 14 to about 25 µg.

In another embodiment, the amount of said antisense oligonucleotide to be administrated per eye per day is from about 16 to about 20 µg.

In one embodiment of the invention, said pharmaceutical composition is to be administrated as drops of 50 µl per eye. It is generally acknowledged that, when a pharmaceutical composition is administrated in the form of an eye drop i.e. 50 µl, only about 10 µl may stay on the eye.

In another embodiment of the invention, said pharmaceutical composition is to be administrated once, twice, three or more times a day.

In one embodiment, said pharmaceutical composition is to be administrated once a day.

In another embodiment, said pharmaceutical composition is to be administrated twice a day, preferably in the morning and in the evening.

According to the invention, the inventors demonstrated that the amount of said antisense oligonucleotide to be administrated per eye per day is from about 20 to 100 µg per drop to stabilize or inhibit the neovascularization.

In one embodiment, the amount of said antisense oligonucleotide to be administrated per eye per day is from about 30 to about 90 µg per drop.

In another embodiment, the amount of said antisense oligonucleotide to be administrated per eye per day is from about 40 to about 90 µg per drop.

In another embodiment, the amount of said antisense oligonucleotide to be administrated per eye per day is from about 50 to about 90 µg per drop.

In another embodiment, the amount of said antisense oligonucleotide to be administrated per eye per day is from about 60 to about 90 µg per drop.

In another embodiment, the amount of said antisense oligonucleotide to be administrated per eye per day is from about 70 to about 90 µg per drop.

In another embodiment, the amount of said antisense oligonucleotide to be administrated per eye per day is from about 80 to about 90 µg per drop.

In one embodiment, the amount of said antisense oligonucleotide to be administrated per eye per day is from about 40 to about 50 µg, preferably about 43 µg: for example, 20 to 25 µg per drop with an administration of 2 drops per eye per day.

In another embodiment, the amount of said antisense oligonucleotide to be administrated per eye per day is from about 80 to about 100 µg, preferably about 86 µg: for example, 40 to 50 µg per drop with an administration of 2 drops per eye per day.

In said embodiment, the pharmaceutical composition is preferably in the form of a unit dose for administering from about 80 to 100 µg, preferably about 86 µg, of said antisense oligonucleotide per eye per day.

For example, two drops of 50 µl of a composition comprising 0.80 to 1 mg/ml of said antisense oligonucleotide are administrated per eye in one time to the subject in need thereof. In another example, one drop of 50 µl of a composition comprising 1.60 to 2 mg/ml of said antisense oligonucleotide is administrated per eye to the subject in need thereof.

In another example, one drop of 50 µl of a composition comprising 0.80 to 1 mg/ml of said antisense oligonucleotide is administrated per eye twice a day to the subject in need thereof.

The pharmaceutical composition of the invention as described here above is for preventing, stabilizing and/or inhibiting the blood and lymph vascularization.

In one embodiment, said pharmaceutical composition as described here above is for treating corneal graft rejection. In one embodiment, the pharmaceutical composition of the invention is indicated for reducing the risk of immune rejections after corneal grafting.

In another embodiment, said pharmaceutical composition as described here above is for treating glaucoma. In one embodiment, glaucoma is selected in the group of primary open angle glaucoma (POAG), primary angle closure glaucoma, normal tension glaucoma (NTG), pediatric glaucoma, pseudoexfoliative glaucoma, pigmentary glaucoma, traumatic glaucoma, neovascular glaucoma, irido corneal endothelial glaucoma. Primary open angle glaucoma is also known as chronic open angle glaucoma, chronic simple glaucoma, glaucoma simplex.

Normal tension glaucoma is also known as low tension glaucoma. Primary angle closure glaucoma is also known as primary closed-angle glaucoma, narrow-angle glaucoma, pupil-block glaucoma, acute congestive glaucoma. Pediatric glaucoma include congenital glaucoma, infantile glaucoma and juvenile glaucoma. Secondary glaucoma include pseudoexfoliative glaucoma, also known as exfoliation glaucoma or glaucoma capsulare, pigmentary glaucoma, traumatic glaucoma, neovascular glaucoma, irido corneal endothelial glaucoma.

In another embodiment, said pharmaceutical composition as described here above is for treating retinopathy, especially diabetic retinopathy and retinopathy of prematurity.

In another embodiment, said pharmaceutical composition as described here above is for treating age related macular degeneration.

EXAMPLES

Figure 1:
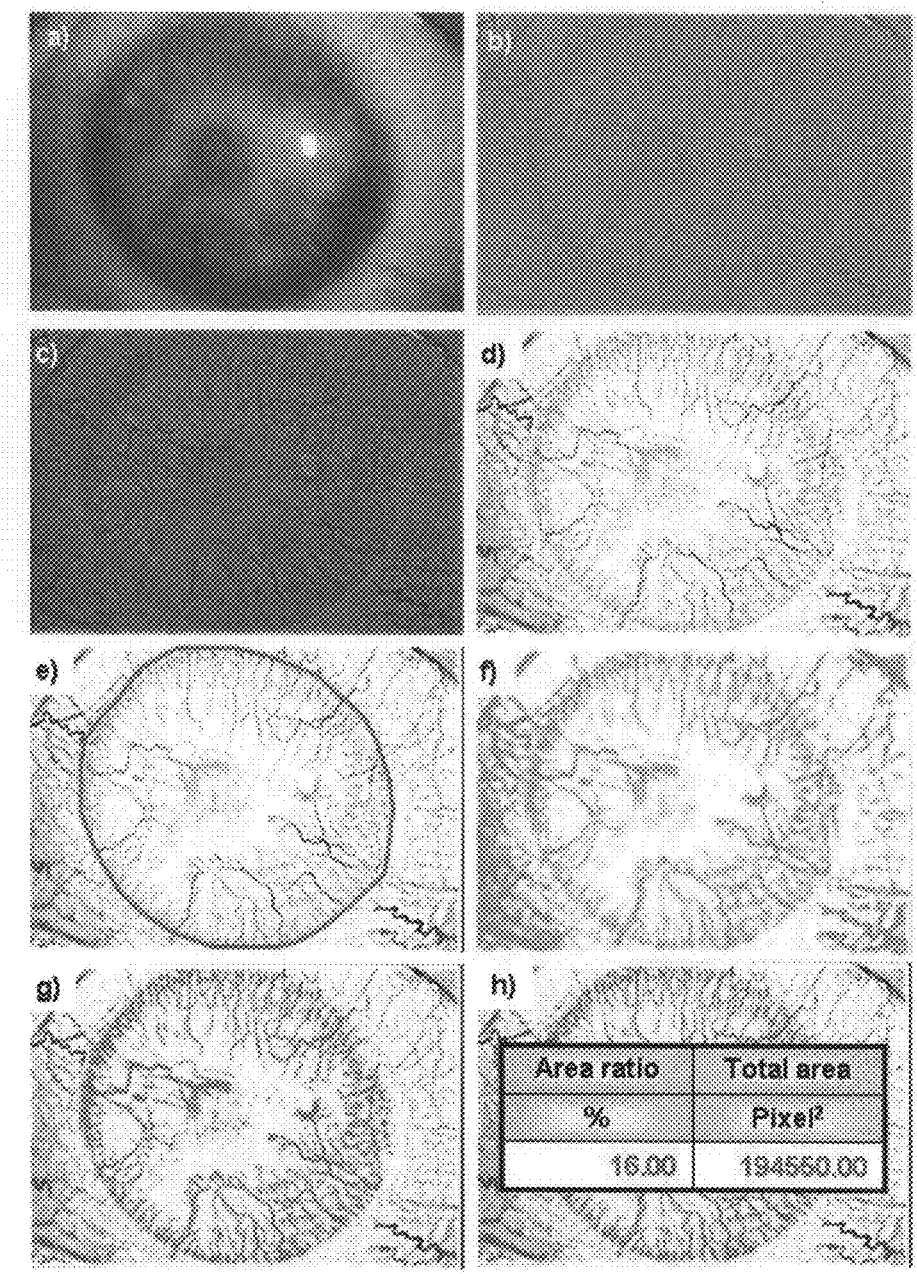
FIG. 1. Image analysis of corneal neovascularization from digitized slit-lamp pictures a) Original image of patient picture; b) the original image was shading-adjusted to balance inhomogeneous illumination; c) the shading-corrected image was separated into the red, green and blue phases, and the green phase was subtracted from the red phase to enhance contrast; d) contrast and shading were optimized again in the subtracted image; e) to detect the vessels, the region of interest (ROI) was first set along the limbus (red circle); f) the gray value range was then adjusted, including the dark vessels, and excluding the brighter background; g) the area defined by threshold setting was measured and h) calculated (total area in pixel$^2$) and normalized to the total ROI (area ratio in %).

The following non limiting examples illustrates certain aspects of the present invention

Example 1

Patients and Methods
Participants

The ongoing phase II study is a 6-month, double-blind, randomized, placebo-controlled trial of GS-101 eye drops to define efficacy and optimal dose in the treatment of progressive corneal neovascularization in men and women suffering from keratitis or keratouveitis of infectious, inflammatory or traumatic origin. Progression of neovascularization was documented during a period of at least 2 weeks and up to 3 months prior to inclusion (as documented by at least 2 photos of the injured cornea) of all participants.

Neovascularization was linked to contact lens misuse in 7 patients (17.5%), pseudomonas keratitis in 2 patients (5%), herpes simplex keratitis in 7 patients (17.5%), herpes zoster keratitis in 1 patient (2.5%), Fuchs-Stevens-Johnson syndrome in 2 patients (5%), other immunologic diseases in 4 patients (10%), prior surgery in 2 patients (5%), alkali burns in 9 patients (22.5%), graft rejection in 5 patients (12.5%), degenerative disorders in 1 patient (2.5%).

An institutional review board for each of the participating institutions approved the study. Participants provided written informed consent before study participation. The study was performed according to the Declaration of Helsinki and ICH Good Clinical Practice standards. This trial was registered under the following number in the Eudract database: 2004-005015-29 with the Protocol Code Number GS101-P2-CG.

Study Design

Eligible participants were randomly assigned to receive GS-101 (43, 86 or 172 µg/day as 2 eye drops, one in the morning and one in the evening) or placebo (2 eye drops, one in the morning and one in the evening; vehicle was used as control). Random assignment was performed by pre-allocated blocks (of 8 patients) to study centres; there was no stratification. All patients and study personnel were blinded to treatment assignments. All patients continued the standard therapy when appropriate (i.e. the ongoing local or systemic therapy for the corneal disease patients were suffering from). In case of bilateral lesion, only one eye was treated with GS-101 eye drops.

The primary end point for this phase II study is the efficacy of the test compound (I.e. inhibition and regression of pathologic corneal neovascularization) and secondary end points are visual acuity and safety of the treatment. In a protocol-specified interim analysis of the first 40 participants, change in the rate of corneal neovascularization was assessed in order to obtain insight on the tolerability and safety of the compound in patients with a damaged cornea. Thirteen participants (33%) were excluded from the interim efficacy analysis because of non-compliance to the treatment (2), non-analysable pictures (4), data not available (4) or adverse events (3) (in contrast, all patients were included for the safety analysis). The strict application of the study protocol was responsible for the exclusion of the majority of these cases. The number of excluded patients was similar between all study groups. These patients are, however, included in the safety analysis. The efficacy variables for this interim analysis were the change in the corneal area invaded by neovessels from baseline to month 3.

Image Analysis and End Point Criteria

Pictures of the cornea were taken at baseline and at week 4 and month 3. The standardized conditions and technical modalities for these photographs are described in the protocol and below. The photos assessing neovascularization were analysed blindly by semi-quantitative measurement and computerized morphometry at the central laboratory (Corneal Angiogenesis Laboratory, Dept. of Opthalmology, Friedrich Alexander University Erlangen-Nürnberg, Erlangen, Germany). The extent of corneal neovascularization was determined by repeatedly performed standardized digital slit-lamp pictures, which were then analyzed morphometrically using image analysis software based on grey filter sampling (Cell: Olympus Soft Imaging Solutions GmbH, Münster, Germany; FIG. 1). Specifically, standardized corneal slit-lamp pictures were digitized and modified by filters as follows: 1) Shading adjustment to balance inhomogeneous illumination; 2) The colour picture was separated into the red, green and blue phase; 3) Green phase was subtracted from red phase to enhance contrast and 4) contrast and shading were optimized. To detect the vessels, first the region of interest (ROI) was set along the limbus, the gray value range was then adjusted, including the dark vessels and excluding the brighter background. The area defined by threshold setting was calculated and normalized to the total ROI (expressed as a percentage covered by blood vessels). A detailed description of the method for animal use was recently published.

Evolution of corneal neovascularization was analyzed as a continuous variable and also as a categorical variable where the dynamic of neovascularization was dichotomized as <<progression>> or <<regression>>. Regression was considered clinically significant if the area of corneal neovascularization measured at baseline was reduced by more than 10% at evaluation time. The exact criteria used to dichotomize progression are as follows:

Progression: (Vascularized area at evaluation time)>[(Vascularized area at baseline)−(10% from vascularized area at baseline)]

Regression: (Vascularized area at evaluation time)<[(Vascularized area at baseline)−(10% from vascularized area at baseline)]

On screening and at each visit onward, a complete ophthalmic assessment was performed by the investigator. This included visual acuity (expressed on a 10° scale), corneal sensitivity, slit lamp biomicroscopy (cornea, iris, lens and vitreous), fluorescein staining test (search for corneal ulcerations and epithelial defects) and intraocular pressure (IOP).

Statistical Analysis

Statistical analyses were performed with SAS release 9.1 (SAS Institute Inc., Cary, N.C., USA) and were conducted blindly using coded groups A, B, C and D according to the protocol. The unit of analysis was the patient, since even in case of bilateral lesions, only one eye was treated.

Because the interim analysis allowed for an early look at efficacy data, the alpha level was adjusted: the interim analysis was conducted at a significance level of 0.015. This yielded a significance level of 0.0414 for the final analysis.

The progression of corneal neovascularization was analyzed using an analysis of covariance (ANCOVA) model with a term for group (A, B, C, D) and cell area at baseline as a covariate. This model was used to estimate progression within each group and to compare the mean progression between the four groups. In the presence of a statistical difference between groups at the significance level of 0.015, the statistical blind was uncovered and pair-wise comparisons versus placebo were conducted with a significance level of 0.005 (0.015/3).

Considering the small sample size, the four groups were also compared using a Fisher exact test. The four groups were compared as categorical variable using a Fisher's exact test, which is more accurate than the chi-squared test when the expected numbers are small. In the presence of a statistical difference between groups at the significance level of 0.015, the statistical blind was uncovered, and pair-wise comparisons vs. placebo were conducted using the Fisher exact test with a significance level of 0.005 (0.015/3).

Results

The interim analysis included 40 participants between January 2006 and June 2007, assigned to receive either placebo (n=10) or GS-101 (n=10 per group; 3 different concentrations). Thirteen participants (33%) were excluded from the interim analysis (see methods and patients section). The remaining 27 patients constitute the patient population of this interim analysis. Baseline characteristics were similar between the groups (Table 1).

Following the ANCOVA analysis, Fisher exact tests were performed on the evolution of neovascularization as categorical variable ("progression" or "regression"). Calculation showed that there was a significant statistical difference between all groups (p=0.015). Blinding was uncovered in order to conduct pair-wise comparisons of each active treat-

TABLE 1

Baseline demographics and neovascularized corneal area.

| Baseline data | | Group 43 μg/d (0.43 mg/ml) (n = 6) | Group 86 μg/d (0.86 mg/ml) (n = 7) | Group 172 μg/d (1.72 mg/ml) (n = 8) | Placebo (n = 6) |
|---|---|---|---|---|---|
| Age | Mean ± SD | 44.7 ± 11.5 | 38.9 ± 18.4 | 51.8 ± 23.9 | 42.7 ± 8.4 |
| | Median | 42.5 | 36.0 | 50.0 | 40.50 |
| | Q1, Q3 | 37.0, 48.8 | 22.5, 54.0 | 33.5, 72.5 | 36.5, 46.0 |
| | Min, Max | 33, 64 | 19, 64 | 19, 81 | 35, 57 |
| Gender | Male (%) | 4 (66.7%) | 6 (85.7%) | 6 (75%) | 5 (83.3%) |
| | Female (%) | 2 (33.3%) | 1 (14.3%) | 2 (25%) | 1 (16.7%) |
| Vascularized area at baseline (% of total corneal area) | Mean ± SD | 8.88 ± 4.09 | 8.92 ± 5.38 | 8.13 ± 3.06 | 9.87 ± 6.99 |
| | Median | 8.03 | 6.57 | 7.47 | 9.41 |
| | Q1, Q3 | 5.55, 11.20 | 4.62, 11.93 | 6.15, 9.45 | 3.37, 13.94 |
| | Min, Max | 4.87, 15.61 | 4.87, 18.96 | 4.47, 14.42 | 3.09, 19.75 |
| Vascularized area at 3 months (% of total corneal area) | Mean ± SD | 8.94 ± 6.23 | 6.87 ± 6.01 | 9.74 ± 8.42 | 10.71 ± 6.40 |
| | Median | 7.73 | 5.09 | 6.70 | 9.51 |
| | Q1, Q3 | 4.58, 9.47 | 2.60, 10.37 | 5.22, 15.57 | 4.98, 17.85 |
| | Min, Max | 3.36, 20.81 | 1.63, 18.83 | 0.06, 22.83 | 4.54, 17.88 |

SD: standard deviation; Q1; Q3: first and third quartile.

Adverse events were reported for all 40 patients. A total of 57 adverse events were reported. The adverse events were of mild (68%), moderate (25%) and severe (7%) intensity. Three adverse events (5.5%) in 3 patients were considered as possibly related to the study products by the investigators and one of these adverse events ("painful eye and pressure sensation" in patient 01-001) led to study drug interruption. Sensation of ocular pain and pressure disappeared after interruption of the treatment. Eight adverse events in 6 patients were classified as serious according to standard definitions of serious adverse events. All of these serious adverse events were assessed as not related to the study drug.

Figure 2:
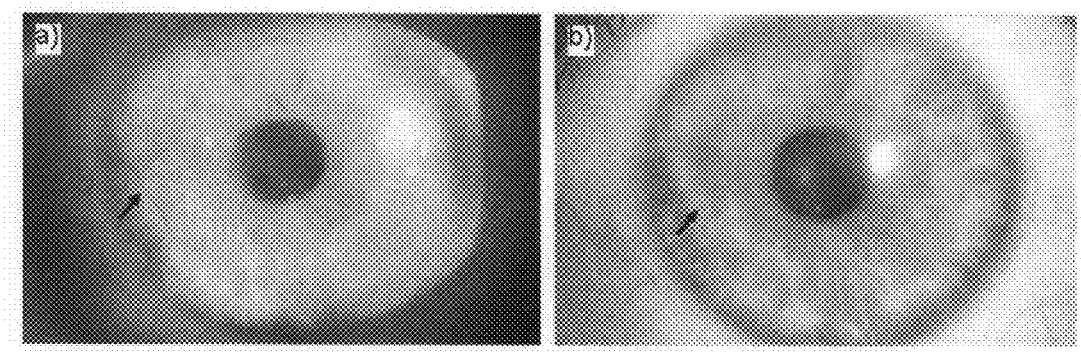
FIG. 2. GS-101 eye drops twice daily inhibited corneal neovascularisation. a) Baseline picture before GS-101 therapy; h) Visit 3-picture after 3 months of treatment; arrows indicate vascularized area.

The overall progression of corneal neovascularization (Table 2) was assessed using an analysis of covariance (ANCOVA) model with one term for the treatment group and for the cell area at visit 1 (baseline). This model provides estimates of progression within each group and compares progression between the four groups. The comparison of the four groups yields a p-value of 0.1256, which failed to reach the significance level of 0.015 required for this interim analysis.

ment group versus placebo using the Fisher exact test with a significance level of 0.005 (namely: 0.015/3) as stated in the protocol. Comparing the ratio of regression and progression of neovascularization among the groups revealed that at a dosage of 86 μg GS-101 daily corneal neovascularization regressed significantly (p=0.0047) (Table 3, FIG. 2).

TABLE 3

Fisher exact tests on the evolution of neovascularization under topical treatmendt with GS101 eye drops versus placebo.

| | Neovascularization | | | |
|---|---|---|---|---|
| | Group 43 μg/d (0.43 mg/ml) (n = 6) | Group 86 μg/d (0.86 mg/ml) (n = 7) | Group 172 μg/d (1.72 mg/ml) (n = 8) | Placebo n = 6 |
| Progression n (%) | 4 (66.7) | 1 (14.3) | 5 (62.5) | 6 (100) |

TABLE 2

Main efficacy variable: cell area progression after 3 months of treatment and ANCOVA parameters.

| Baseline vs. 3-month variation | | Group 43 μg/d (0.43 mg/ml) (n = 6) | Group 86 μg/d (0.86 mg/ml) (n = 7) | Group 172 μg/d (1.72 mg/ml) (n = 8) | Placebo (n = 6) |
|---|---|---|---|---|---|
| Change in vascularized area (% of total corneal area) | Mean ± SD | +0.07 ± 2.94 | −2.04 ± 1.57 | +1.60 ± 7.63 | +0.89 ± 2.15 |
| | Median | −0.17 | −1.55 | −0.30 | +0.64 |
| | Q1, Q3 | −2.19, +0.96 | −2.99, −0.70 | −3.73, +6.76 | −0.65, +2.65 |
| | Min, Max | −3.22, +5.19 | −4.77, −0.13 | −6.08, +13.41 | −1.90, +3.94 |
| ANCOVA P = 0.1256 | Estimated progression | +0.0661 | −2.042 | +1.624 | +0.855 |
| | S.E. | 1.180 | 0.607 | 2.699 | 0.962 |
| | 95% C.I. | −3.022, 3.154 | −3.560, −0.524 | −4.754, 8.001 | −1.806, 3.515 |

C.I.: confidence interval; S.E.: standard error; SD: standard deviation; Q1; Q3: first and third quartile.

TABLE 3-continued

Fisher exact tests on the evolution of neovascularization
under topical treatmendt with GS101 eye drops versus placebo.

| | Neovascularization | | | |
|---|---|---|---|---|
| | Group 43 µg/d (0.43 mg/ml) (n = 6) | Group 86 µg/d (0.86 mg/ml) (n = 7) | Group 172 µg/d (1.72 mg/ml) (n = 8) | Placebo n = 6 |
| Regression n (%) | 2 (33.3) | 6 (85.7) | 3 (37.5) | 0 (0) |
| P value | 0.4545 | 0.0047 | 0.2088 | |

Furthermore, the two other doses of GS-101 tested appeared active, although the differences observed did not reached statistical significance, i.e. p=0.4545 for the group treated with 43 µg daily and p=0.2088 for the group treated with 172 µg daily. With the lower concentration of GS-101, progression of corneal neovascularization tended to stabilize as revealed by both the mean (0.07±2.94) and median (−0.17) changes in neovascularization area (Table 2). Surprisingly, in the high dose GS-101 (172 µg daily) group, an apparent progression (mean=1.60±7.63) of corneal neovascularization was seen. Further analysis showed 2 outliers as seen by the large inter quartile range and the wide min-max range (Table 2), which were caused by 2 non-responding patients. By excluding the data of these 2 patients a similar regression of corneal neovascularization to the GS-101 86 µg group was obtained.

Although not subjected to analysis at this time of the study, the mid-treatment data on visual acuity suggest an improvement in patients under active treatment.

Discussion

The demonstration that GS-101 eye drops stopped progression of corneal neovascularisation and even induced regression of newly outgrowing blood vessels in the interim analysis of this phase II trial is therefore of great therapeutic interest. Even more since the safety data suggest the eye drops to be well tolerated.

Example 2

Formulations of GS101 Compositions

Emulsions:

| Phases | composition | % masse |
|---|---|---|
| A | Caprilic acid and capric mix: Miglyol 812N | 8.00 |
| A | Glyceryl Stearate and PEG-75 1: Gelot 64 | 3.50 |
| A | Cetylic alcohol | 2.00 |
| B | Carbomer: Carbopol 980 NF | 0.05 |
| B | Purified H2O | Qsp 100% (61.99) |
| C | 10% NaOH Solution | Qsp pH 7 (0.29) |
| D | Glycerol | 5.00 |
| D | Urea | 4.00 |
| E | GS101 | 0.172* |
| E | Purified H2O | 15.00 |
| A | Caprilic acid and capric mix: Miglyol 812N | 8.00 |
| A | Glyceryl Stearate and PEG-75 1: Gelot 64 | 3.50 |
| A | Cetylic alcohol | 2.00 |
| B | Carbomer: Carbopol 980 NF | 0.05 |
| B | Purified H2O | Qsp 100% (66.06) |
| C | 10% NaOH Solution | Qsp pH 7 (0.22) |
| D | Glycerol | 5.00 |
| E | GS101 | 0.172* |
| E | Purified H2O | 15.00 |

* with purity (97.36%) and water content (8.31%): 192.68 mg

Ointment:

| composition | % masse |
|---|---|
| GS101 | 0.172* |
| Paraffin oil | 60.03 |
| Vaseline oil | 39.80 |

*with purity (94.65%) and water content (8.4%): 198.38 mg

Collyre:

| composition | % masse |
|---|---|
| GS101 | 0.086* |
| NaCl 0.9% | Qsp 100% |

*with purity (96.4%) and water content (5.21%): 94.1 mg

The invention claimed is:

1. A pharmaceutical composition, comprising as active agent an antisense oligonucleotide having the sequence SEQ ID NO: 1 or any function-conservative sequence comprising from 9 to 30 nucleotides,
   wherein said function-conservative sequence has at least 75% sequence identity compared to SEQ ID NO: 1 and conserves a capacity to inhibit IRS-1 gene expression, said function-conservative sequence comprises the sequence SEQ ID NO: 20, and
said antisense oligonucleotide is present in the composition at a concentration of from about 0.40 mg/ml to about 2 mg/ml.

2. The pharmaceutical composition according to claim 1, wherein said antisense oligonucleotide is in a concentration from about 0.80 mg/ml to about 1 mg/ml.

3. The pharmaceutical composition according to claim 1, wherein said pharmaceutical composition is in a form of an aqueous solution, a suspension, a gel, an ointment, micelles or an emulsion.

4. The pharmaceutical composition according to claim 1, wherein said pharmaceutical composition is in a form to be administrated topically, by intravitreal injection or by intraconjunctivial injection.

5. The pharmaceutical composition according to claim 1, wherein said pharmaceutical composition is in a form to be administrated as an eye drop once, twice, or more per day.

6. The pharmaceutical composition according to claim 5, wherein the amount of said antisense oligonucleotide to be administrated daily per eye is from about 40 µg to about 100 µg per drop.

7. The pharmaceutical composition according to a claim 1, wherein the antisense oligonucleotide is in a form to be administrated daily to an eye in an amount of from about 8 µg to about 40 µg.

8. A unit dose container comprising the pharmaceutical composition according to claim 1.

9. The unit dose container according to claim 8, capable of dispensing eye drops.

10. A method for treating corneal graft rejection, comprising administering to a subject in need thereof a composition comprising as active agent, an antisense oligonucleotide having the sequence SEQ ID NO: 1 or any function-conservative sequence comprising from 9 to 30 nucleotides,
wherein said function-conservative sequence has at least 75% sequence identity compared to SEQ ID NO: 1 and conserves a capacity to inhibit IRS-1 gene expression,
said function-conservative sequence comprises the sequence SEQ ID NO: 20, and
said antisense oligonucleotide is present in the composition at a concentration of from about 0.40 mg/ml to about 2 mg/ml.

11. A method for reducing the risk of immune rejection after corneal grafting, comprising administering to a subject in need thereof a composition comprising as active agent, an antisense oligonucleotide having the sequence SEQ ID NO: 1 or any function-conservative sequence comprising from 9 to 30 nucleotides,
wherein said function-conservative sequence has at least 75% sequence identity compared to SEQ ID NO: 1 and conserves a capacity to inhibit IRS-1 gene expression,
said function-conservative sequence comprises the sequence SEQ ID NO: 20, and
said antisense oligonucleotide is present in the composition at a concentration of from about 0.40 mg/ml to about 2 mg/ml.

12. A method for treating glaucoma, comprising administering to a subject in need thereof a composition comprising as active agent, an antisense oligonucleotide having the sequence SEQ ID NO: 1 or any function-conservative sequence comprising from 9 to 30 nucleotides,
wherein said function-conservative sequence has at least 75% sequence identity compared to SEQ ID NO: 1 and conserves a capacity to inhibit IRS-1 gene expression,
said function-conservative sequence comprises the sequence SEQ ID NO: 20, and
said antisense oligonucleotide is present in the composition at a concentration of from about 0.40 mg/ml to about 2 mg/ml.

13. The method according to claim 12, wherein glaucoma is selected from the group consisting of: primary open angle glaucoma (POAG), primary angle closure glaucoma, normal tension glaucoma (NTG), pediatric glaucoma, pseudoexfoliative glaucoma, pigmentary glaucoma, traumatic glaucoma, neovascular glaucoma, and irido corneal endothelial glaucoma.

14. A method for treating retinopathy, comprising administering to a subject in need thereof a composition comprising as active agent, an antisense oligonucleotide having the sequence SEQ ID NO: 1 or any function-conservative sequence comprising from 9 to 30 nucleotides,
wherein said function-conservative sequence has at least 75% sequence identity compared to SEQ ID NO: 1 and conserves a capacity to inhibit IRS-1 gene expression,
said function-conservative sequence comprises the sequence SEQ ID NO: 20, and
said antisense oligonucleotide is present in the composition at a concentration of from about 0.40 mg/ml to about 2 mg/ml.

15. A method for treating age related macular degeneration, comprising administering to a subject in need thereof a composition comprising as active agent, an antisense oligonucleotide having the sequence SEQ ID NO: 1 or any function-conservative sequence comprising from 9 to 30 nucleotides,
wherein said function-conservative sequence has at least 75% sequence identity compared to SEQ ID NO: 1 and conserves a capacity to inhibit IRS-1 gene expression,
said function-conservative sequence comprises the sequence SEQ ID NO: 20, and
said antisense oligonucleotide is present in the composition at a concentration of from about 0.40 mg/ml to about 2 mg/ml.

16. A method for treating, stabilizing and/or inhibiting blood and lymph vascularization, comprising administering to a subject in need thereof an effective amount of the pharmaceutical composition according to claim 1.

17. The pharmaceutical composition according to claim 1, wherein the antisense oligonucleotide comprises 9 to 30 nucleotides of SEQ ID NO: 1 and inhibits IRS-1 gene expression.

18. The pharmaceutical composition according to claim 1, wherein the antisense oligonucleotide consists of 9 to 30 nucleotides of SEQ ID NO: 1 and inhibits IRS-1 gene expression.

19. The pharmaceutical composition according to claim 1, wherein the antisense oligonucleotide comprises 12 to 30 nucleotides, comprises SEQ ID NO: 20, and inhibits IRS-1 gene expression.

20. The pharmaceutical composition according to claim 1, wherein the antisense oligonucleotide comprises 25 to 30 nucleotides, comprises SEQ ID NO: 1, and inhibits IRS-1 gene expression.

* * * * *